(12) United States Patent
Zilbershtein et al.

(10) Patent No.: US 10,099,970 B2
(45) Date of Patent: Oct. 16, 2018

(54) METHODS OF PREPARING OLIGOMERS OF AN OLEFIN

(71) Applicant: PUBLIC JOINT STOCK COMPANY "SIBUR HOLDING", Tobolsk (RU)

(72) Inventors: Timur Mikhailovich Zilbershtein, Kazan (RU); Denis Alekseevich Lenev, Khimki (RU)

(73) Assignee: PUBLIC JOINT STOCK COMPANY "SIBUR HOLDING", Tobolsk (RU)

( * ) Notice: Subject to any disclaimer, the term of this patent is extended or adjusted under 35 U.S.C. 154(b) by 0 days.

(21) Appl. No.: 15/539,113

(22) PCT Filed: Dec. 23, 2014

(86) PCT No.: PCT/RU2014/000974
§ 371 (c)(1),
(2) Date: Jun. 22, 2017

(87) PCT Pub. No.: WO2016/105228
PCT Pub. Date: Jun. 30, 2016

(65) Prior Publication Data
US 2017/0355652 A1    Dec. 14, 2017

(51) Int. Cl.
*C07C 2/32* (2006.01)
*C08F 110/02* (2006.01)
(Continued)

(52) U.S. Cl.
CPC .............. *C07C 2/32* (2013.01); *B01J 31/143* (2013.01); *B01J 31/1825* (2013.01);
(Continued)

(58) Field of Classification Search
None
See application file for complete search history.

(56) References Cited

U.S. PATENT DOCUMENTS

| 6,133,495 A | 10/2000 | Urata et al. |
| 7,718,838 B2 | 5/2010 | Woodard et al. |

(Continued)

FOREIGN PATENT DOCUMENTS

| CN | 103 102 237 | 2/2015 |
| CN | 102558107 | 4/2015 |

(Continued)

OTHER PUBLICATIONS

International Search Report and Written Opinion dated Sep. 18, 2015, directed to International Application No. PCT/RU2014/000974; 8 pages.

(Continued)

*Primary Examiner* — Catherine S Branch
(74) *Attorney, Agent, or Firm* — Morrison & Foerster LLP

(57) ABSTRACT

Methods of preparing oligomers of an olefin are provided. The methods can include providing a composition that includes an alkylaluminum compound, a chromium compound, and a hydrocarbon solvent. The hydrocarbon solvent can include n-undecane, a C8-C11 alkane compound having one branch, or a mixture thereof. The methods can further include contacting an olefin with the composition to form oligomers of the olefin. The olefin can include ethylene, and the oligomers of the olefin can include 1-hexene.

23 Claims, 1 Drawing Sheet

(51) Int. Cl.
    *B01J 31/14*     (2006.01)
    *B01J 31/18*     (2006.01)

(52) U.S. Cl.
    CPC ......... *C08F 110/02* (2013.01); *B01J 2231/12* (2013.01); *B01J 2231/20* (2013.01); *B01J 2531/62* (2013.01); *C07C 2531/14* (2013.01); *C07C 2531/22* (2013.01)

(56) References Cited

U.S. PATENT DOCUMENTS

| | | |
|---|---|---|
| 2012/0302715 A1 | 11/2012 | Zilbershtein et al. |
| 2013/0102826 A1 | 4/2013 | Lattner et al. |
| 2013/0144024 A1* | 6/2013 | Lattner .................. B01J 8/005 526/352 |

FOREIGN PATENT DOCUMENTS

| | | |
|---|---|---|
| EP | 0 668 105 | 8/1995 |
| EP | 2 098 543 | 9/2009 |
| FR | 1 308 672 | 11/1962 |
| WO | WO-2016/105226 | 6/2016 |
| WO | WO-2016/105227 | 6/2016 |

OTHER PUBLICATIONS

McDaniel, M. P. (Jul. 2010). "A Review of the Phillips Supported Chromium Catalyst and Its Commercial Use for Ethylene Polymerization" Chapter 3 in *Advances in Catalysis*, vol. 53. B. Gates ed., Academic Press, pp. 123-606.

\* cited by examiner

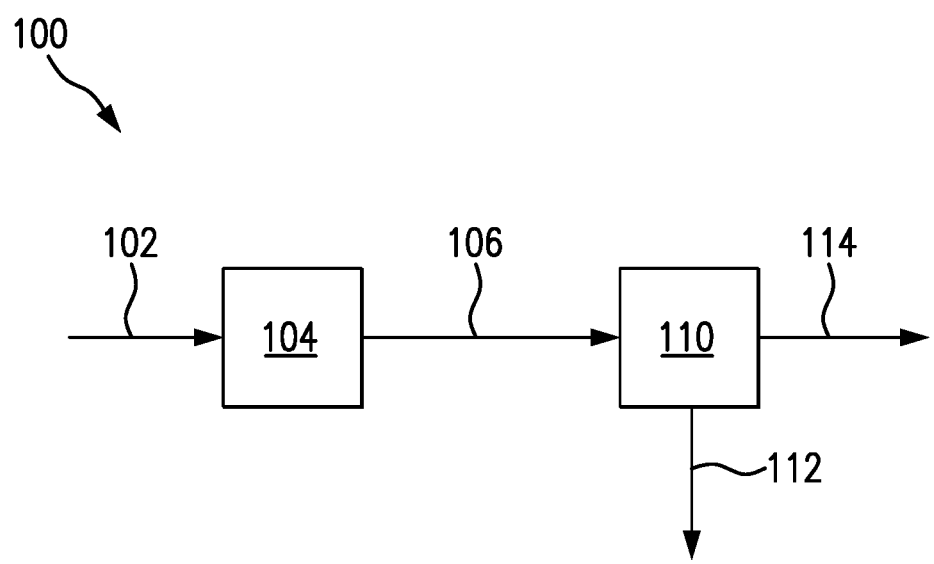

METHODS OF PREPARING OLIGOMERS OF AN OLEFIN

REFERENCE TO RELATED APPLICATIONS

This application is a national stage application under 35 USC 371 of International Application No. PCT/RU2014/000974, filed Dec. 23, 2014, the entire contents of which are incorporated herein by reference.

BACKGROUND OF THE INVENTION

Field of the Disclosed Subject Matter

The presently disclosed subject matter relates to methods of preparing oligomers of an olefin. For example, the presently disclosed subject matter provides methods of preparing 1-hexene from ethylene. The methods can include the use of particular hydrocarbon solvents, e.g., n-undecane and/or a C8-C11 alkane compound having one branch.

Description of Related Art

Oligomerization of olefins can produce many valuable chemical products. For example, simple feedstock olefins can be oligomerized to provide useful higher olefins. Industrially important processes include the preparation of alpha olefins (α olefins) from ethylene, e.g., the preparation of 1-hexene via trimerization of ethylene.

A problem encountered in some oligomerizations of olefins can be incomplete selectivity for the desired oligomer. That is, in addition to the desired oligomer, some side products and byproducts can be formed. The side products and byproducts can include other oligomers as well as polymers. As an example, in oligomerization of ethylene to 1-hexene, other isomers of hexene (e.g., 2-hexene and 3-hexene) can be formed, as well as higher oligomers of ethylene (e.g., octene, decene, and dodecene) and polyethylene.

Polymers formed as side products and byproducts during oligomerization of olefins can be problematic. Polymer that remains dissolved in a product mixture must be separated from the desired oligomer product. Moreover, polymers can impair process performance. For example, on industrial scale, polymer can deposit on internal parts of oligomerization reactors and/or product pipelines as well as other equipment that comes into contact with reaction and product mixtures. Removal of polymer deposits can require shutdown of process equipment for days or weeks and can require substantial effort, which can include steaming of the polymer, treatment with water to peel the polymer from equipment surfaces, and physical removal of the polymer.

As an example, in oligomerization of ethylene to 1-hexene, polyethylene can deposit on reactors and downstream equipment and can complicate purification of 1-hexene. It can therefore be beneficial to discourage deposition of polyethylene and to facilitate removal of polyethylene from a product stream from an ethylene trimerization reaction.

Olefin oligomerization reactions can be conducted in hydrocarbon solvents. For example, in some existing processes for preparation of 1-hexene from ethylene, C6-C7 alkanes (including cycloalkanes) are used as solvents. Known solvents include cyclohexane, methylcyclohexane, and heptane. Such solvents can have advantageous properties (e.g., good solubility of organometallic catalysts) but also tend to have boiling points similar to that of 1-hexene, which can make separation of 1-hexene from the solvent difficult.

Various attempts have been made to use other hydrocarbon solvents in olefin oligomerization reactions. For example, U.S. Patent Publication No. 2013/0144024, European Patent No. EP0668105, Chinese Patent Application Publication No. CN102558107, Chinese Patent Application Publication No. CN103102237, European Patent Application Publication No. EP2098543, and U.S. Patent Publication No. 2013/0102826, each of which is hereby incorporated by reference in its entirety, variously describe use of linear and branched C5-C12 alkane solvents for preparation of 1-hexene from ethylene. However, the C8-C11 branched alkanes described in the prior art as solvents for olefin oligomerization reactions are alkanes with multiple branches, e.g., isooctane (2,2,4-trimethylpentane). The prior art generally suggests that higher (C8 and above) alkane solvents have inferior solubility properties as compared to C6 and C7 solvents. Furthermore, the prior art generally suggests that cyclic alkane solvents are better able to dissolve organometallic catalysts and side product polymers than linear hydrocarbons, and that linear hydrocarbons are better able to dissolve organometallic catalysts and side product polymers than branched hydrocarbons. See also M. P. McDaniel, Advances in Catalysis, 2010, Vol. 53. Changes in solvent composition are known to have unpredictable effects on catalyst activity, as described in U.S. Pat. No. 7,718,838, which is hereby incorporated by reference in its entirety.

There remains a need for methods of preparing oligomers of an olefin with reduced deposition of polymer side products and easier separation of polymer from oligomer products. It is therefore desirable to provide solvents for olefin oligomerization that achieve improved catalyst solubility, improved catalyst activity, improved polymer solubility, improved separation of polymer, and improved separation of oligomer product.

SUMMARY OF THE INVENTION

The purpose and advantages of the disclosed subject matter will be set forth in and apparent from the description that follows, as well as will be learned by practice of the disclosed subject matter. Additional advantages of the disclosed subject matter will be realized and attained by the methods and techniques particularly pointed out in the written description and the claims hereof, as well as from the appended drawing.

To achieve these and other advantages and in accordance with the purpose of the disclosed subject matter, as embodied and broadly described, the disclosed subject matter provides methods of preparing oligomers of an olefin, including methods of preparing 1-hexene from ethylene.

In accordance with the disclosed subject matter, methods of preparing oligomers of an olefin are provided. An exemplary method can include providing a composition that includes an alkylaluminum compound, a chromium compound, and a solvent. The solvent can include one or more solvents such as C8-C11 alkane compounds having one branch, n-undecane, and combinations thereof. The method can further include contacting an olefin with the composition to provide a solution that includes oligomers of the olefin. In some embodiments, the solution can have a cloud point of less than 75° C.

An additional exemplary method of preparing oligomers of an olefin can include providing a composition including an alkylaluminum compound, a chromium compound, and a hydrocarbon solvent. The method can further include contacting an olefin with the composition to provide a solution that includes oligomers of the olefin. The solution can have a cloud point of less than 75° C.

For example, and as embodied herein, the alkylaluminum compound can include an irradiated alkylaluminum compound. Furthermore, the olefin can include ethylene. Additionally, methods of preparing oligomers of an olefin can include contacting the olefin and the composition with hydrogen. In some embodiments, the oligomers of the olefin can include 1-hexene.

In some embodiments, the solution can include a polymer. The polymer can be polyethylene. The polyethylene can have a melting point of less than 125.4° C.

In some embodiments, the C8-C11 alkane compound having one branch can include an isomer of decane. The isomer of decane can be one or more of 2-methylnonane, 3-methylnonane, 4-methylnonane, 5-methylnonane, 3-ethyloctane, 4-ethyloctane, and 4-propylheptane. In some embodiments, the solvent can include at least 50%, by volume, of the C8-C11 alkane compound having one branch or at least 80%, by volume, of the C8-C11 alkane compound having one branch. In other embodiments, the solvent can include at least 50%, by volume, of n-undecane or at least 90%, by volume, of n-undecane.

The disclosed subject matter also provides methods of preparing 1-hexene. An exemplary method can include providing a composition that includes an alkylaluminum compound, a chromium compound, and a hydrocarbon solvent. The method can further include contacting ethylene with the composition to provide a solution that includes 1-hexene and polyethylene. The polyethylene can have a melting point of less than 125.4° C.

It is to be understood that both the foregoing general description and the following detailed description are exemplary and are intended to provide further explanation of the disclosed subject matter claimed.

The accompanying drawing, which is incorporated in and constitutes part of this specification, is included to illustrate and provide a further understanding of the disclosed subject matter. Together with the description, the drawing serves to explain the principles of the disclosed subject matter.

BRIEF DESCRIPTION OF THE DRAWING

FIG. 1 is a schematic representation illustrating an exemplary system that can be used in conjunction with the methods of the disclosed subject matter.

While the disclosed subject matter is described below in detail with reference to the FIGURE, it is done so in connection with the illustrative embodiments and not by way of limitation.

DETAILED DESCRIPTION OF THE INVENTION

The methods presented herein can be used for various oligomerization processes, including, but not limited to, olefin oligomerizations, e.g., trimerization or tetramerization of ethylene. The methods can be used on relatively small scale, e.g., laboratory scale or bench scale, and can be used on relatively large scale, e.g., industrial scale. Oligomerization can occur in a homogeneous or colloidal solution. Oligomerization can occur in various reactors known in the art, as described in more detail below. Oligomerization can occur in more than one reactor operated in series or parallel. For purpose of illustration only and not limitation, and as embodied herein, the methods presented can be used in the context of trimerization of ethylene to 1-hexene.

As used herein, the term "alkyl" refers to saturated aliphatic groups. Alkyl groups can be straight chain (e.g., ethyl, n-propyl, n-butyl) or branched chain (e.g., i-propyl, s-butyl). The term "alkyl" also encompasses cycloalkyl groups, i.e., saturated aliphatic carbon-based cyclic groups. Cycloalkyl groups can include one ring or more than one ring. By way of non-limiting example, cycloalkyl groups can include cyclopropyl, cyclobutyl, cyclopentyl, cyclohexyl, cycloheptyl, and cyclooctyl.

As used herein, the terms "alkane" and "alkanes" refer to saturated aliphatic compounds. Alkyl compounds can be straight chain (e.g., ethane, propane, n-butane, n-hexane, n-octane, n-decane, n-undecane) or branched chain (e.g., i-butane, 3-methylnonane). Straight chain alkanes are also known as linear alkanes or n-alkanes and are acyclic alkanes without side chains. Branched chain alkanes, also known simply as "branched alkanes," are acyclic, non-linear alkanes with one or more side chains.

An alkane compound having one branch is an alkane with exactly one side chain in addition to the main chain. Also known as the root chain, the main chain is the longest continuous chain of carbon atoms in an alkane compound. An alkane compound having one branch can also be termed "an alkane compound with one branch" or a "monobranched alkane." Exemplary alkane compounds with one branch include i-butane, i-pentane, and 2-methylnonane. Alkane compounds having one branch can be distinguished from alkane compounds having more than one branch. Exemplary alkane compounds having more than one branch include neopentane and isooctane (2,2,4-trimethylpentane).

As used herein, the terms "alkane" and "alkanes" also encompass cycloalkane compounds, i.e., saturated aliphatic carbon-based cyclic compounds. Cycloalkanes can include one ring or more than one ring. By way of non-limiting example, cycloalkanes can include cyclopropane, cyclobutane, cyclopentane, cyclohexane, cycloheptane, cyclooctane, cyclononane, and cyclodecane. Cycloalkanes can be substituted. Exemplary substituted cycloalkanes include methylcyclopentane and methylcyclohexane.

As used herein, the term "halogen" refers to the Group 17 elements, i.e., fluorine, chlorine, bromine, iodine, and astatine.

As used herein, the terms "group" and "moiety" refer to parts of a larger composition, compound, molecule, or structure.

As used herein, the term "cloud point" refers to the temperature below which a fluid containing dissolved solids becomes turbid or cloudy. At temperatures below the cloud point, dissolved solids are no longer completely soluble and can separate out of the solution, forming a distinct precipitate phase, which can give the solution a cloudy appearance.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In accordance with the disclosed subject matter, methods of preparing oligomers of an olefin can generally include providing a composition that includes an alkylaluminum compound, a chromium compound, and a hydrocarbon solvent. In some embodiments, the hydrocarbon solvent can include a C8-C11 alkane compound having one branch, n-undecane, or a combination thereof. The method can further include contacting an olefin with the composition to form oligomers of the olefin. In some embodiments, the olefin can include ethylene and the oligomers of the olefin can include 1-hexene.

Reference will now be made in detail to the various exemplary embodiments of the disclosed subject matter, exemplary embodiments of which are illustrated in the accompanying drawing. The methods and corresponding techniques of the disclosed subject matter will be described in conjunction with the detailed description.

The accompanying FIGURE serves to further illustrate various embodiments and to explain various principles and advantages all in accordance with the disclosed subject matter. For purpose of explanation and illustration, and not limitation, exemplary embodiments of the methods of preparing oligomers of an olefin in accordance with the disclosed subject matter are shown in conjunction with FIG. 1. While the presently disclosed subject matter is described with respect to the system of FIG. 1 and the Examples presented below, one skilled in the art will recognize that the disclosed subject matter is not limited to the illustrative embodiments, and that the methods and techniques described herein can be used to prepare oligomers of an olefin in any suitable reaction or system.

According to the disclosed subject matter, with reference to FIG. 1, the presently disclosed methods can be performed in conjunction with an exemplary system 100. The system 100 can include a reactor 104 in which an olefin oligomerization reaction can be conducted. The reactor 104 can be coupled to one or more feed lines 102. While one feed line 102 is shown in FIG. 1, it should be understood that multiple feed lines can be coupled to the reactor 104. The feed line(s) 102 can feed various components to the reactor 104. In some embodiments, the components fed to the reactor 104 can include an organometallic catalyst, a transition metal source, an alkylaluminum compound, a zinc compound, a pyrrole compound, an olefin, hydrogen, and/or one or more solvents. By way of non-limiting example, there can be one or more feed lines feeding an organometallic catalyst solution, one or more feed lines feeding solvent(s), one or more feed lines feeding an olefin (e.g., ethylene), and/or one or more feed lines feeding hydrogen. In some embodiments, more than one hydrocarbon compound can be used as solvent, and different mixtures of solvent can be used to prepare various compositions. For example, a first solvent (e.g., n-octane) can be used as a catalyst solvent (e.g., a solvent used to dissolve an alkylaluminum compound, a chromium compound, and additional catalyst components) and a second solvent can be added as an additional reaction solvent. All solvents can be combined in the reactor 104 to provide a combined reaction solvent.

An olefin oligomerization reaction can occur in the reactor 104, to provide oligomerization products as well as side product polymer. An effluent stream 106 containing oligomerization products (i.e., oligomers of the olefin) as well as side product polymer and organometallic catalyst can be removed from the reactor 104. In some embodiments, the effluent stream 106 can be cooled. In some embodiments, a deactivating agent (e.g., water) and/or a sorbent can be added to the effluent stream 106. Further description of sorbents that can be used in accordance with the disclosed subject matter is provided in International (PCT) Application No. PCT/RU2014/000972, filed on the same day as the present application, which is hereby incorporated by reference in its entirety. A deactivating agent can deactivate the organometallic catalyst to provide a deactivated catalyst. Cooling the effluent stream 106, adding a deactivating agent, and/or adding a sorbent can precipitate polymer as well as deactivated catalyst. Precipitate containing sorbent, polymer, and/or deactivated catalyst can optionally be separated in a separation unit 110, to provide precipitate 112 and a purified product stream 114.

The olefin oligomerization reactions of the presently disclosed subject matter can be performed in various reactors known in the art. By way of non-limiting example, suitable reactors 104 can include continuous stirred-tank reactors, batch reactors, plug flow reactors, and pipe or tubular reactors (laminar flow reactors). The reactor 104 can be a reactor suitable for gas/liquid reactions, e.g., an autoclave reactor with an agitator, a bubble column reactor (bubbling reactor) with straight-flow or counter-flow gas and liquid supply, or a bubbling gas lift reactor. The reactor can include components and accessories not depicted in FIG. 1, such as, for example, one or more additional feed lines, one or more gas inlet lines, one or more gas outlet lines, one or more flue gas exhaust lines, one or more agitators, a reaction zone, one or more heating elements, and/or one or more viscometers. The components and accessories can be placed at various locations on the reactor, as known in the art.

In some embodiments, the organometallic catalyst in the reactor 104 can include one or more transition metal sources. By way of non-limiting example, the transition metal(s) can include Ti, Zr, Hf, Ni, Cr, Fe, Co, Pd, Pt, and combinations thereof. In accordance with the disclosed subject matter, the organometallic catalyst can include chromium (Cr). The organometallic catalyst can be a homogenous catalyst or a heterogeneous catalyst.

When the organometallic catalyst includes chromium, the source of chromium can be organic chromium compounds and/or inorganic chromium compounds. The oxidation state of the chromium source can vary. For example, chromium sources can include compounds in which chromium is in the oxidation states 0, +1, +2, +3, +4, +5, and +6. Generally, the chromium source can be a chromium compound of the formula $CrX_n$, where the X substituents are the same or different and where n is a number from 1 to 6. The X substituents can be organic or inorganic radicals. By way of non-limiting example, suitable organic radicals X can include from 1 to 20 carbon atoms and can include alkyl groups, alkoxy groups, carboxy groups, acetylacetonate groups, amino groups, and amido groups. By way of non-limiting example, suitable inorganic radicals X can include halogens (to form a chromium halide), sulfate (to form a chromium sulfate), and oxygen (to form a chromium oxide). Examples of chromium sources can include chromium(III) chloride, chromium(III) acetate, chromium(III) tris-ethylhexanoate, chromium(III) acetylacetonate, chromium(III) pyrrolide, chromium(II) acetate, and chromyl chloride $(CrO_2Cl_2)$.

The organometallic catalyst in the reactor 104 can further include an alkylaluminum compound. In some embodiments, the alkylaluminum compound can be an activator of a transition metal-based catalyst center (e.g., a chromium center). Alkylaluminum compounds can include halogenated alkylaluminum compounds, alkoxyalkylaluminum compounds, and mixtures thereof. Alkylaluminum compounds are compounds that include at least one aluminum-alkyl bond and, in some nonlimiting embodiments, can be represented by the general formulas $AlR_3$, $AlR_2X$, $AlRX_2$, $AlR_2OR$, $AlRXOR$, or $Al_2R_3X_3$, where R is an alkyl group and X is a halogen atom (e.g., Cl or Br). Nonlimiting examples of alkylaluminum compounds include trimethylaluminum, triethylaluminum, tripropylaluminum, tributylaluminum, diethylaluminum chloride, ethylaluminum dichloride, ethylaluminum sesquichloride, and methylaluminoxane (MAO). Alkylaluminum compounds can be used as mixtures of multiple alkylaluminum compounds. In some embodiments, the alkylaluminum compound can be triethylaluminum or a mixture of triethylaluminum and diethylaluminum chloride.

In accordance with the disclosed subject matter, one or more components of the organometallic catalyst in the reactor 104 can be irradiated. In some embodiments, the alkylaluminum compound can be an irradiated alkylaluminum compound. Alkylaluminum compounds can be irradiated to increase their activity and to increase the overall activity of the organometallic catalyst in the reactor 104. In some embodiments, the irradiation can be microwave irradiation. Microwave irradiation of alkylaluminum compounds is generally described in United States Patent Publication No. 2012/0302715, the contents of which are hereby incorporated by reference in their entirety. By way of non-limiting example, one or more alkylaluminum compounds can be irradiated with microwave radiation of a frequency between about 0.2 GHz and 20 GHz. In some embodiments, the microwave radiation can have a frequency of about 2.45 GHz. The duration of irradiation can be between about 0.5 minutes (30 seconds) and about 20 minutes. In some embodiments, one or more alkylaluminum compounds can be irradiated with microwave radiation prior to mixing with other components of the catalyst composition (e.g., a transition metal source). If the alkylaluminum compound is irradiated prior to mixing with other components of the catalyst composition, it can be important to limit the time that elapses between irradiation and mixing. For example, the time can be less than 10 minutes, less than 5, or less than 3 minutes. In some embodiments, the time between irradiation of the alkylaluminum compound and mixing with other components of the catalyst composition (e.g., a transition metal source) can be less than 3 minutes. In other embodiments, one or more alkylaluminum compounds can first be combined with a transition metal source (e.g., a chromium source) and a pyrrole compound to provide a composition, and the composition can then be irradiated as described above. Further description of irradiation of alkylaluminum compounds and other catalyst components, in accordance with the disclosed subject matter, is provided in International (PCT) Application No. PCT/RU2014/000973, filed on the same day as the present application, which is hereby incorporated by reference in its entirety.

The organometallic catalyst in the reactor 104 can further include one or more halogenic compounds. The halogenic compound can be described as a halide source. The halogenic compounds can be compounds of formula $R_mX_n$, wherein R is an organic, organometallic, or inorganic radical, X is a halogen (e.g., F, Cl, Br, or I), and the sum (m+n) is greater than 0. Exemplary halogenic compounds can include $AlEt_2Cl$, $AlEtCl_2$, $AlCl_3$, dibutylaluminum chloride, diethylaluminum bromide, diethylaluminum iodide, butyl bromide, dichloromethane, carbon tetrachloride, $CHCl_3$ (chloroform), hexachloroethane, boron trichloride, and germanium tetrachloride. Addition of one or more halogenic compounds can improve the selectivity, activity, and/or productivity of the organometallic catalyst.

The organometallic catalyst in the reactor 104 can further include a zinc compound. In some embodiments, the zinc compound can be an activator of a transition metal-based catalyst center (e.g., a chromium center). In some embodiments, the zinc compound can include metallic zinc (Zn(0)), zinc-copper couples, alkylzinc compounds (including dialkylzinc compounds), arylzinc compounds (including diarylzinc compounds), zinc amides (e.g., zinc pyrrolides or zinc porphyrin complexes), zinc oxygenates (e.g., zinc formates, zinc acetates, zinc 2-ethylhexanoates, and other zinc carboxylates), zinc halides (e.g., anhydrous zinc chloride), and combinations thereof. In some embodiments, the zinc compound can include a dialkylzinc compound. The dialkylzinc compound can include dimethylzinc, diethylzinc, dibutylzinc, and mixtures thereof. In some embodiments, the zinc compound can include a diarylzinc compound. The diarylzinc compound can include diphenylzinc, ditolylzinc, and mixtures thereof. Further description of zinc compounds, in accordance with the disclosed subject matter, is provided in International (PCT) Application No. PCT/RU2014/000973, filed on the same day as the present application, which is hereby incorporated by reference in its entirety.

The organometallic catalyst in the reactor 104 can further include a pyrrole compound. In some embodiments, the pyrrole compound can coordinate to a transition metal and serve as a ligand. The pyrrole compound can be a compound that includes a pyrrole moiety, i.e., a five-membered aromatic heterocycle that contains a single nitrogen atom. By way of non-limiting example, pyrrole compounds include pyrrole, 2,5-dimethylpyrrole, lithium pyrrolide ($C_4H_4NLi$), 2-ethylpyrrole, indole, 2-methylindole, and 4,5,6,7-tetrahydroindole. In some embodiments, the pyrrole compound can be pyrrole or 2,5-dimethylpyrrole.

The organometallic catalyst in the reactor 104 can be varied, as is understood in the art. For example, when an alkylaluminum compound, a chromium compound, and a pyrrole compound are used, the molar ratios of aluminum to chromium and pyrrole compound to chromium can be varied. For example, and as embodied herein, the aluminum to chromium ratio can vary from about 10:1 to about 2000:1, e.g., from about 20:1 to about 300:1. For example, and as embodied herein, the pyrrole compound to chromium ratio can vary from about 2:1 to about 100:1, e.g., from about 3:1 to about 7:1. For example, and as embodied herein, the ratio of any additional halogenic compound to chromium can vary from about 1:1 to about 150:1, e.g., from about 8:1 to about 16:1, as calculated on the basis of elemental halogen. A zinc compound may or may not be included.

Olefins useful for olefin oligomerization can include simple feedstock olefins, e.g., ethylene (ethene), propylene (propene), and butylene (butene). In some embodiments, the olefin can be ethylene. Olefins can be oligomerized to provide useful higher olefins. Industrially important processes include preparation of alpha olefins (α olefins) from ethylene. Alpha olefins are olefin compounds with a carbon-carbon double bond (C=C) at the primary or alpha position. Alpha olefins prepared from oligomerization can include various $C_5$-$C_{40}$ olefins and mixtures thereof. For example, alpha olefins prepared from oligomerization can include 1-pentene, 1-hexene, 1-heptene, 1-octene, 1-nonene, 1-decene, 1-undecene, 1-dodecene, 1-tridecene, 1-tetradecene, higher alpha olefins, and mixtures thereof. In accordance with the disclosed subject matter, the olefin oligomerization reaction can include a trimerization of ethylene to 1-hexene.

When the olefin oligomerization in the reactor 104 is a trimerization of ethylene to 1-hexene, the pressure of ethylene used is variable, as is understood in the art. For example, and as embodied herein, the ethylene pressure can be varied between about 1 to about 200 bar. In some embodiments, the ethylene pressure can be greater than 4 bar. In some embodiments, in can be advantageous to increase the ethylene pressure to increase the rate of oligomerization.

In some embodiments of the presently disclosed subject matter, the temperature with the reactor 104 can be between about 0° C. and about 160° C. The temperature within the reactor 104 can be between about 40° C. and about 120° C. For example, when the olefin oligomerization in the reactor 104 is a trimerization of ethylene to 1-hexene, the temperature of the reactor can be between about 40° C. and about 120° C., e.g., at about 100° C. In some embodiments, and as described herein, it can be advantageous to maintain a reaction temperature above about 80° C., e.g., above about 95° C. At such temperatures, polymer side products (e.g., polyethylene) can remain fully dissolved in the solvent and the organometallic catalyst can remain active and selective. By way of non-limiting example, in some trimerization reactions of ethylene to 1-hexene, lower temperatures (e.g., temperatures below about 80° C.) can cause polyethylene to precipitate from solution.

In accordance with the disclosed subject matter, reaction time can be varied as understood in the art. The reaction time can be defined as the residence time of the feedstock and solvent in the oligomerization reaction zone. In the case of continuous flow reactors, the reaction time can be the mean residence time, as understood in the art. The reaction time can vary depending on olefin used, reaction temperature, reaction pressure, and other parameters of the reaction. In some embodiments, the reaction can be terminated in less than a day. In some embodiments, reaction time can be shorter than a day, e.g., less than 12 hours, less than 6 hours, less than 3 hours, less than 2 hours, less than 1 hour, less than 30 minutes, less than 15 minutes, less than 10 minutes, less than 5 minutes, less than 3 minutes, less than 2 minutes, less than 1 minute, less than 30 seconds, less than 15 seconds, less than 10 seconds, less than 5 seconds, less than 3 seconds, or about 1 second.

In accordance with the disclosed subject matter, an olefin and a catalyst composition (e.g., a composition that includes an alkylaluminum compound, a chromium compound, and a hydrocarbon solvent) can be contacted with hydrogen. Hydrogen can be fed into the reactor 104. In some embodiments, hydrogen can serve as a diluent. Hydrogen can accelerate the oligomerization reaction and/or increase activity of the organometallic catalyst. In some embodiments, hydrogen can reduce the amount of side product polymer formed and limit deposition (precipitation) of polymer with the reactor 104 and in downstream equipment. For example, in the oligomerization of ethylene to 1-hexene, hydrogen can reduce formation of polyethylene and discourage deposition of polyethylene.

One or more solvents can be used in oligomerization of olefins in the reactor 104. The solvent can include one or more hydrocarbon compounds. The hydrocarbon compounds can include alkane compounds, including straight chain alkanes, branched alkanes, and cycloalkanes. The hydrocarbon compounds can also include alkene compounds (e.g., 1-hexene) and/or arene (aromatic) compounds (e.g., benzene, toluene). The hydrocarbon compounds can be a mixture of hydrocarbons, e.g., kerosene. The hydrocarbon compounds can be C4-C12 hydrocarbons. By way of non-limiting example, the solvent can include cyclohexane, methylcyclohexane, heptane (and isomers thereof), cycloheptane, octane (and isomers thereof), cyclooctane, nonane (and isomers thereof), cyclononane, decane (and isomers thereof), cyclodecane, undecane (and isomers thereof), cycloundecane, dodecane (and isomers thereof), cyclododecane, and combinations thereof. In some embodiments, solvents can be preheated prior to use. For example, solvents can be preheated to a temperature approximately equal to the reaction temperature, e.g., about 100° C.

In some embodiments, the solvent can include n-undecane. In some embodiments, the solvent can include one or more C8-C11 alkane compounds having one branch. The C8-C11 alkane compounds having one branch can include isomers of octane, nonane, decane, and undecane. Isomers of octane with one branch can include one or more of 2-methylheptane, 3-methylheptane, 4-methylheptane, and 3-ethylhexane. Isomers of nonane with one branch can include one or more of 2-methyloctane, 3-methyloctane, 4-methyloctane, 3-ethylheptane, and 4-ethylheptane. Isomers of decane with one branch can include one or more of 2-methylnonane, 3-methylnonane, 4-methylnonane, 5-methylnonane, 3-ethyloctane, 4-ethyloctane, and 4-propylheptane. Isomers of undecane with one branch can include 2-methyldecane, 3-methyldecane, 4-methyldecane, 5-methyldecane, 3-ethylnonane, 4-ethylnonane, 5-ethylnonane, and 4-propyloctane. It should be understood that n-undecane and C8-C11 alkane compounds having one branch can be combined with and used as solvents with other hydrocarbon compounds, e.g., linear alkane compounds, alkane compounds having more than branch, and/or cycloalkane compounds.

In some embodiments, the solvent can include at least 50%, by volume, of one or more C8-C11 alkane compounds having one branch. By way of non-limiting example, the solvent can include about 50%, about 60%, about 70%, about 80%, about 90%, about 95%, or about 100% of one or more C8-C11 alkane compounds having one branch.

In some embodiments, the solvent can include at least 50%, by volume, of n-undecane. By way of non-limiting example, the solvent can include about 50%, about 60%, about 70%, about 80%, about 90%, about 95%, or about 100% of n-undecane.

In accordance with the disclosed subject matter, and as described above, in some embodiments a first solvent can be used to dissolve a catalyst composition and an additional solvent can be added to the reactor 104. The first solvent (e.g., n-octane) can be described as a catalyst solvent and the second solvent (e.g., n-undecane, a C8-C11 alkane compound having one branch, or a mixture thereof) can be described as an additional reaction solvent. It should be understood that these solvents will mix and combine in the reactor 104 to provide a combined reaction solvent, such that the first solvent and the second solvent will both be present during the olefin oligomerization reaction. In some embodiments the first solvent (catalyst solvent) and the second solvent can have the same composition.

In accordance with the disclosed subject matter, components of the solvent(s) used can be selected on the basis of their boiling points. For example, alkane compounds having similar boiling points, which can boil within a relatively narrow temperature range (e.g., within about 10° C., about 20° C., about 30° C., or about 40° C.) can be used. Selection of alkane compounds having similar boiling points can facilitate separation, as such compounds can be conveniently distilled away from desired olefin oligomerization products (e.g., 1-hexene). Various mixtures of alkane compounds with similar boiling points can be commercially available, e.g., EXXSOL™ (EXXONMOBIL™) and ISOPAR™ (EXXONMOBIL™).

By way of non-limiting example, when a chromium-containing organometallic catalyst is used, the amount of solvent can be adjusted such that the concentration of chromium in the reaction mixture is approximately 1-10 mg per 100 mL solvent, e.g., about 5 mg per 100 mL.

In accordance with the disclosed subject matter, various components present in the reactor 104 can be mixed in any order. By way of non-limiting example, an alkylaluminum compound can be mixed with a halogenic compound in a first hydrocarbon solvent to provide a first composition. The first mixture can be mixed with a transition metal source (e.g., a chromium source) and a pyrrole compound in a second hydrocarbon solvent to provide a second composition, which can serve as an organometallic catalyst. The first hydrocarbon solvent and the second hydrocarbon solvent can be the same or different. An olefin can then be contacted with the second composition to form oligomers of the olefin. Alternatively, the second composition can be further diluted in a third hydrocarbon solvent to provide a third composition, and an olefin can be contacted with the third composition.

In accordance with the disclosed subject matter, olefin oligomerization reactions can be conducted in the absence of water and oxygen. For example, water and oxygen can be excluded from the reactor 104.

In accordance with the disclosed subject matter, the effluent stream 106 from the olefin oligomerization reaction can include an organometallic catalyst, various products, byproducts, and side products from the olefin oligomerization reaction, and one or more solvents. The effluent stream can include polymers.

In accordance with the presently disclosed subject matter, polymers formed during olefin oligomerization can include polymers of the olefin being oligomerized. For example, polyethylene can form during oligomerization of ethylene. Polyethylene can be insoluble in the reaction solvent and can deposit on internal parts of oligomerization reactors and/or product pipelines, as well as other equipment that comes into contact with reaction and product mixtures. Moreover, polymer that remains dissolved in an oligomerization product mixture can require separation from the desired oligomer product.

One or more deactivating agents can be added to the effluent stream 106. Suitable deactivating agents known to one of skill in the art can be used, including water, alcohols, amines, amino alcohols, and combinations thereof. Exemplary alcohols can include methanol, ethanol, n-propanol, i-propanol, n-butanol, i-butanol, t-butanol, 2-butanol, 2-ethylhexanol, and combinations thereof. Exemplary amines can include ammonia, methylamine, dimethylamine, trimethylamine, ethylamine, diethylamine, triethylamine, tri-n-propylamine, diisopropylethylamine, tri-n-butylamine, piperazine, pyridine, ethylenediamine, diethylenetriamine, and combinations thereof. Exemplary amino alcohols can include ethanolamine, diethanolamine, triethanolamine, methyldiethanolamine, dodecyldiethanolamine, 1-amino-2-propanol, and combinations thereof. In accordance with the disclosed subject matter, the deactivating agent can be water.

In some embodiments, the effluent stream 106 can be cooled. Cooling the effluent stream can include removing the effluent stream from a heat source, e.g., removing the effluent stream from a heated reactor. Cooling the effluent stream can also include passing the effluent stream through a cooling unit, e.g., a heat exchanger. Cooling the effluent stream can include mixing a hot effluent stream with a cooled effluent stream. Cooling the effluent stream can include cooling the effluent stream to a temperature in a range between 100° C. and 20° C., e.g., to less than about 95° C., about 90° C., about 85° C., about 80° C., about 75° C., about 70° C., about 65° C., about 60° C., about 55° C., about 50° C., about 45° C., about 40° C., about 35° C., about 30° C., or about 25° C. Cooling the effluent stream can include cooling the effluent stream to ambient temperature, e.g., to a temperature in a range from about 20° C. to about 25° C. Cooling the effluent stream can include exposing the effluent stream to air. In some embodiments, the effluent stream can be cooled to a temperature between about 70° C. and about 20° C. The temperature to which the effluent stream is cooled can be selected to induce precipitation of the polymer while also avoiding excessive energy consumption during the cooling process. By way of non-limiting example, the effluent stream can be cooled from about 110° C. to about 70° C. in a settler-cooler, via recycling in a loop cooling stream with a temperature of about 40° C. and a residence time in the settler-cooler of about 1 hour.

In accordance with the disclosed subject matter, the methods of precipitating polymer and deactivated organometallic catalyst in an olefin oligomerization reaction can further include separating the precipitate from the effluent stream 106 to provide a purified product 114. Separation can provide separated precipitate 112 as well as the purified product 114. Separation can be performed via a separation unit 110. In some embodiments, the effluent stream can be cooled in the separation unit 110. In some embodiments, the separation unit can be one or more settling tanks, centrifugal separators, or filters, or a combination thereof. For example, and as embodied herein, precipitate can be concentrated in one or more settling tanks and periodically unloaded. Centrifugal separators can also be used to separate precipitate, with or without earlier concentration. Filtration can also be used to separate precipitate, with or without earlier concentration.

By way of non-limiting example, the effluent stream 106 can be cooled and solids (e.g., polymer) settled under pressure. The effluent stream can then be filtered and sent to a deethenizer column, which can remove ethylene and hydrogen and send them to a recycling compressor. The filtered and degassed effluent can then be sent to a product isolation column, where 1-hexene can be distilled and isolated as the top product. Heavier compounds, including solvent and higher olefins, can be removed from the bottom of the product isolation column.

In some embodiments of the presently disclosed subject matter, olefin oligomerization reactions can be conducted in a solvent that includes n-undecane, a C8-C11 alkane compound having one branch, or a combination thereof. It has been found that such compounds can have surprising and unexpected advantages when used as solvents as compared to cycloalkane compounds as well as highly branched alkane compounds.

It has surprisingly been found that n-undecane and C8-C11 alkane compounds having one branch can provide improved solubility of the organometallic catalyst as well as side product polymer. Use of n-undecane and C8-C11 alkane compounds having one branch as reaction solvents can also reduce formation of polymer side product and provide polymer with improved solubility.

For example, as shown in the Examples described below, n-undecane and C10 alkane compounds having one branch (e.g., a mixture of 4-ethyloctane and 5-methylnonane) were improved solvents for reactions in which polyethylene forms as a side product, providing solutions with a cloud point of less than 75° C. By contrast, using cyclohexane and isooctane as solvents for reactions in which polyethylene forms as a side product provided solutions with a cloud point of 80° C. or higher. Because polyethylene can remain soluble even at relatively low temperatures (e.g., temperatures between about 75° C. and about 80° C.) in solutions that include n-undecane and/or C8-C11 alkane compounds having one branch, polyethylene is less likely to precipitate and deposit within the reactor and downstream equipment. Reduced precipitation can improve operational efficiency and reduce downtime associated with occlusion of reactor equipment and clogging of lines, valves, and pumps. Polyethylene can be conveniently precipitated upon cooling of the effluent stream 106, e.g., by cooling to a temperature below the cloud point of the solution.

Moreover, as shown in the Examples, the polyethylene side product formed during oligomerization of ethylene to 1-hexene in solvents that include n-undecane and C10 alkane compounds having one branch (4-ethyloctane and 5-methylnonane) can have improved solubility and a lower melting point as compared to polyethylene side product formed during oligomerization of ethylene to 1-hexene in solvents that primarily contain cyclohexane or isooctane. In some embodiments, the polyethylene formed can have a melting point of less than 125.4° C. Use of an irradiated alkylaluminum compound can improve the catalytic activity of the organometallic catalyst and help to lower the melting point of the polyethylene formed.

Without being bound to any particular theory, it may be that use of a solvent that includes n-undecane, a C8-C11 alkane compound having one branch, or a combination thereof can affect catalytic activity. For example, use of a solvent that includes n-undecane, a C8-C11 alkane compound having one branch, or a combination thereof may encourage transfer and branch termination reactions productive for olefin oligomerization while discouraging unproductive polymer chain growth reactions.

n-Undecane, C8-C11 alkane compounds having one branch, and other C8-C11 alkane isomers can have boiling points similar to one another (e.g., in a range from about 100° C. to about 200° C.) but substantially higher than the boiling points of lower alkenes. For example, n-undecane, C8-C11 alkane compounds having one branch, and other C8-C11 alkane isomers can have boiling points substantially higher than 1-hexene (63° C.). The substantial difference in boiling points can simplify separation of solvent from 1-hexene by distillation. At the same time, the boiling points of n-undecane, C8-C11 alkane compounds having one branch, and other C8-C11 alkane isomers can be lower than higher hydrocarbons (e.g., n-dodecane, which has a boiling point of 214-218° C.). Lower boiling points can reduce the amount of energy required for distillation, improving overall economic efficiency and reducing environmental impact of the methods of the presently disclosed subject matter.

The presently disclosed subject matter can provide improved cloud points of reaction mixtures (effluent streams), e.g., cloud points that are lower than the boiling points of the solvents. By way of non-limiting example, and as shown in the Examples, when trimerization of ethylene is conducted in solvents containing n-undecane or C10 alkanes having one branch, it is possible to remove an effluent stream containing 1-hexene and dissolved polyethylene from the reactor without inducing immediate precipitation and deposition. The effluent stream can subsequently be cooled to below the cloud point of the solution to precipitate polyethylene, which can then be removed conveniently.

EXAMPLES

The presently disclosed subject matter will be better understood by reference to the following Examples, which are provided as exemplary and not by way of limitation.

Example 1

Catalyst Preparation

1.A. Method A (with Microwave Irradiation):
An organometallic catalyst composition was prepared according to the following procedure. A mixture of 100 g of a 25% solution of triethylaluminum in hexane (by weight) and 80 g of 15% solution of diethylaluminum chloride in hexane (by weight) was passed at a rate of 20 g/minute through a MARS 6 microwave source chamber with the magnetron switched on, via a 100 ml PTFE tube in the microwave source chamber, and added to a mixture of 3.50 g of 2,5-dimethylpyrrole and 3.50 g of anhydrous chromium (III) ethylhexanoate in 200 ml of ethylbenzene. The resulting mixture was diluted with cyclohexane up to 750 ml.

1.B. Method B (without Microwave Irradiation):
An organometallic catalyst composition was prepared according to the following procedure. A mixture of 100 g of 25% solution of triethylaluminum in hexane and 80 g of 15% solution of diethylaluminum chloride in hexane was added to a mixture of 3.50 g of 2,5-dimethylpyrrole and 3.50 g of anhydrous chromium(III) ethylhexanoate in 200 ml of ethylbenzene. The resulting mixture was diluted with cyclohexane up to 750 ml.

Example 2

Trimerization of Ethylene to 1-Hexene with Cyclohexane as Reaction Solvent

2.A. Example A (with Irradiated Alkylaluminum Compound):
An oligomerization reaction (trimerization) of ethylene to provide 1-hexene was conducted as follows. A 0.3 l steel reactor equipped with a heating/cooling jacket, an agitator, and gas and liquid inputs was provided. To the reactor, 0.1 l (100 ml) of cyclohexane and 1.0 ml of the catalyst solution prepared using Method A (as described in Example 1) were added. 200 ml of hydrogen was then dosed to the reactor. The agitator was started at a speed of 800 rpm. The mixture was heated to 100° C., and this temperature was maintained during the reaction. Ethylene was then dosed until the reactor pressure reached 14 bar. Thereafter, additional ethylene was dosed so that a pressure of 14 bar was maintained throughout the reaction. After 360 minutes (6 hours), the ethylene feed was shut off. The reactor was depressurized through the discharge line to 3 bar. The reactor contents were then quickly unloaded through a bottom valve. After unloading the hot solution (effluent stream) from the reactor, polymer precipitated in the form of bulky fibrous sediment. Some polymer was also wound around the agitator and adhered to the walls and bottom of the reactor. The polymer was collected, washed with isopropanol, hydrochloric acid, dried in vacuum (1 mbar) at 80° C. for 8 hours, and then subjected to analysis. The remaining solution of the effluent stream was analyzed using gas chromatography. The results are presented in Table 1.

2.B. Example B (with Non-Irradiated Alkylaluminum Compound):
An oligomerization reaction (trimerization) of ethylene to provide 1-hexene was conducted as follows. The same procedure presented in Example 2.A was followed, except that the catalyst was prepared using Method B (as described in Example 1). Visually, the effluent stream and polymer formed did not differ from Example 2.A. The polymer and the remaining solution of the effluent stream were analyzed as in Example 2.A, and the results of analysis are presented in Table 1.

Example 3

Trimerization of Ethylene to 1-Hexene with n-Undecane as Reaction Solvent

3.A. Example A (with Irradiated Alkylaluminum Compound):

Preparation of the Catalyst (with Microwave Irradiation):

An organometallic catalyst composition was prepared according to the following procedure. A mixture of 100 g of a 25% solution of triethylaluminum in hexane and 80 g of 15% solution of diethylaluminum chloride in hexane was passed at the rate of 20 g/minute through a MARS 6 microwave source chamber with the magnetron switched on, via a 100 ml PTFE tube in the microwave source chamber and added to a mixture of 3.50 g of 2,5-dimethylpyrrole and 3.50 g of anhydrous chromium (III) ethylhexanoate in 200 ml of ethylbenzene. The resulting mixture was diluted with n-octane up to 750 ml.

Trimerization of Ethylene:

An oligomerization reaction (trimerization) of ethylene to provide 1-hexene was conducted as follows. A 0.3 l steel reactor equipped with a heating/cooling jacket, an agitator, and gas and liquid inputs was provided. To the reactor, 0.1 l (100 ml) of n-undecane and 1.0 ml of the catalyst solution prepared as described immediately above were added. 200 ml of hydrogen was then dosed to the reactor. The agitator was started at a speed of 800 rpm. The mixture was heated to 100° C., and this temperature was maintained during the reaction. Ethylene was then dosed until the reactor pressure reached 14 bar. Thereafter, additional ethylene was dosed so that a pressure of 14 bar was maintained throughout the reaction. After 360 minutes (6 hours), the ethylene feed was shut off. The reactor was depressurized through the discharge line down to atmospheric pressure. The reactor contents (effluent stream) were drained through a bottom valve into a 250 ml glass flask. The solution (effluent stream) discharged from the reactor was transparent. Upon cooling to 60° C., the solution became cloudy. When the solution was cooled to 25° C., polymer (polyethylene) gradually precipitated in the form of white powder. The inside of the reactor was clean, without traces of polymer. The polymer was separated from the cooled effluent stream and dried. The polymer and the remaining solution of the effluent stream were analyzed as in Example 2.A, and the results of analysis are presented in Table 1.

3.B. Example B (with Non-Irradiated Alkylaluminum Compound):

Preparation of the Catalyst (without Microwave Irradiation):

An organometallic catalyst composition was prepared according to the following procedure. A mixture of 100 g of 25% solution of triethylaluminum in hexane and 80 g of 15% solution of diethylaluminum chloride in hexane was added to a mixture of 3.50 g of 2,5-dimethylpyrrole and 3.50 g of anhydrous chromium (III) ethylhexanoate in 200 ml of ethylbenzene. The resulting mixture was diluted with n-octane up to 750 ml.

Trimerization of Ethylene:

An oligomerization reaction (trimerization) of ethylene to provide 1-hexene was conducted as follows. The same procedure set out in Example 3.A was followed, except that the catalyst was prepared as described immediately above. Visually, the effluent stream and polymer formed were very similar to those of Example 3.A. The polymer and the remaining solution of the effluent stream were analyzed as in Example 2.A, and the results of analysis are presented in Table 1.

Example 4

Trimerization of Ethylene to 1-Hexene in a Reaction Solvent that Includes C10 (Decane) Isomers Having One Branch 4.A. Example A (with Irradiated Alkylaluminum Compound):

Preparation of the Solvent:

A monobranched C10 hydrocarbon solvent mixture was prepared as follows. A mixture of C10 (decane) isomers was prepared by distillation, hydrogenation, and purification of a hydrocarbon mixture. The mixture contained 40% 4-ethyloctane (a monobranched alkane), 50% 5-methylnonane (a monobranched alkane), and 10% n-decane (a linear alkane), by mol %. Accordingly, the mixture contained 90% C10 alkane compounds having one branch. The mixture was used as reaction solvent as described below.

Trimerization of Ethylene:

An oligomerization reaction (trimerization) of ethylene to provide 1-hexene was conducted as follows. A 0.3 l steel reactor equipped with a heating/cooling jacket, an agitator, and gas and liquid inputs was provided. To the reactor, 0.1 l (100 ml) of the hydrocarbon mixture described immediately above and 1.0 ml of the catalyst solution prepared using Method A (as described in Example 1) were added. 200 ml of hydrogen was then dosed to the reactor. The agitator was started at a speed of 800 rpm. The mixture was heated to 100° C., and this temperature was maintained during the reaction. Ethylene was then dosed until the reactor pressure reached 14 bar. Thereafter, additional ethylene was dosed so that a pressure of 14 bar was maintained throughout the reaction. After 360 minutes (6 hours), the ethylene feed was shut off. The reactor was depressurized through the discharge line. The reactor contents were then quickly unloaded through a bottom valve into a 250 ml glass retort. The solution discharge from the reactor was transparent. Upon cooling to 72° C., the solution became cloudy. When the solution was cooled to 25° C., polymer (polyethylene) gradually precipitated in the form of white powder. The inside of the reactor was clean, without any traces of polymer. The polymer in the cooled effluent stream was separated and dried. The polymer and the remaining solution of the effluent stream were analyzed as in Example 2.A, and the results of analysis are presented in Table 1.

4.B. Example B (with Non-Irradiated Alkylaluminum Compound):

Preparation of the Solvent:

A monobranched C10 hydrocarbon solvent mixture was prepared according to the procedure described in Example 4.A.

Trimerization of Ethylene:

An oligomerization reaction (trimerization) of ethylene to provide 1-hexene was conducted as follows. The same procedure presented in Example 4.A was followed, except that the catalyst was prepared using Method B (as described in Example 1). Visually, the total amount of polymer (polyethylene) in the reactor appeared somewhat greater than in Example 4.A. The polymer formed in the cooled effluent stream and the remaining solution of the effluent stream were analyzed as in Example 2.A, and the results of analysis are presented in Table 1.

Example 5

Trimerization of Ethylene to 1-Hexene with Isooctane as Reaction Solvent

5.A. Example A (with Irradiated Alkylaluminum Compound):
Trimerization of Ethylene:

Trimerization of ethylene to form 1-hexene was carried out as in Example 4.A except that isooctane (2,2,4-trimethylpentane) was used as reaction solvent rather than the monobranched C10 hydrocarbon solvent mixture of Example 4.A. The effluent stream discharged from the reactor was cloudy. Upon cooling to 25° C., polymer (polyethylene) gradually precipitated from the effluent stream in the form of white powder. Polymer fibers were observed on the agitator within the reactor. A small amount of polymer was observed adhered to the bottom of the reactor. The polymer isolated as sediment from the cooled effluent stream and the remaining solution of the effluent stream were analyzed as in Example 2.A, and the results of analysis are presented in Table 1.

5.B. Example B (with Non-Irradiated Alkylaluminum Compound):
Trimerization of Ethylene:

Trimerization of ethylene to form 1-hexene was carried out as in Example 4.B except that isooctane (2,2,4-trimethylpentane) was used as reaction solvent rather than the monobranched C10 hydrocarbon solvent mixture of Example 4.B. Upon discharging the hot effluent stream from the reactor, polymer precipitated immediate from the hot solution, in the form of bulky, fibrous sediment. Polymer fibers were observed on the agitator within the reactor as well adhered to the walls and bottom of the reactor. The polymer was separated and dried. The polymer and the remaining solution of the effluent stream were analyzed as in Example 2.A, and the results of analysis are presented in Table 1.

Table 1 compares the results of the ethylene trimerization reactions described in Examples 2-5.

TABLE 1

| Example No. | Irradiated Alkylaluminum? (Y = yes; N = no) | Solvent* | 1-Hexene concentration in the remaining solution of the effluent stream (GC area %) | Cloud point of the effluent stream, ° C. | Polymer melting point (DSC, 2nd melting), ° C. |
|---|---|---|---|---|---|
| 2A | Y | cyC6 | 22.0 | >80 | 133.1 |
| 2B | N | cyC6 | 24.0 | >80 | 134.0 |
| 3A | Y | n-C11 | 5.0 | 60 | 125.2 |
| 3B | N | n-C11 | 3.2 | 60 | 124.8 |
| 4A | Y | i-C10 | 15.0 | 72 | 124.8 |
| 4B | N | i-C10 | 11.8 | 73 | 125.9 |
| 5A | Y | i,i,i-C8 | 21.8 | >100 | 125.4 |
| 5B | N | i,i,i-C8 | 6.2 | >100 | 131.7 |

*cyC6 = cyclohexane;
n-C11 = n-undecane;
i-C10 = mixture of decane isomers described in Example 4;
i,i,i-C8 = isooctane (2,2,4-trimethylpentane)

Polymer melting points were measured using a Netzsch DSC 204 F1 differential microcalorimeter according to ISO 11357-3. Cloud points were determined visually while measuring temperature with a thermometer.

For the purpose of illustration, Table 1 indicates that ethylene trimerization reactions conducted in n-undecane (Example 3) and a solvent containing C10 alkanes having one branch (Example 4) had improved and unexpected properties as compared to ethylene trimerization reactions conducted in cyclohexane (Example 2) and isooctane (Example 5). As shown in Table 1, the cloud point of the effluent stream (reaction mass) removed from the reactor was lower after reaction in n-undecane (Example 3) and solvent containing C10 alkanes having one branch (Example 4) than in the other examples. Lower cloud points indicate that polyethylene polymer remained relatively soluble in n-undecane and the solvent containing C10 alkanes having one branch, preventing precipitation at high temperature. This result was corroborated by visual inspection of the reactors after each trimerization reaction; the reactors in Examples 2 and 5 were visibly contaminated with relatively large quantities of deposited polyethylene whereas the reactors in Examples 3 and 4 contained few or no visible polyethylene deposits.

Use of n-undecane and/or a solvent containing C10 alkanes having one branch can also provide ethylene trimerization reactions wherein the polyethylene formed has a relatively low melting point. In Example 3A, which was conducted in n-undecane with irradiated alkylaluminum compound, the resulting polyethylene had a melting point of 125.2° C. In Example 3B, which was conducted in n-undecane with non-irradiated alkylaluminum compound, the resulting polyethylene had a melting point of 124.8° C. In Example 4A, which was conducted in and a solvent containing C10 alkanes having one branch with irradiated alkylaluminum compound, the resulting polyethylene also had a melting point of 124.8° C. A lower polyethylene melting point can be correlated to higher solubility and reduced likelihood of harmful deposition.

Additional Embodiments

Additionally or alternatively, the disclosed subject matter can include one or more of the following embodiments:

Embodiment 1. A method of preparing oligomers of an olefin, including providing a composition that includes an alkylaluminum compound, a chromium compound, and a solvent selected from the group consisting of C8-C11 alkane compounds having one branch, n-undecane, and combinations thereof and contacting an olefin with the composition to provide a solution that includes oligomers of the olefin.

Embodiment 2. The method of the foregoing Embodiment, wherein the solution has a cloud point of less than 75° C.

Embodiment 3. A method of preparing oligomers of an olefin, including providing a composition that includes an alkylaluminum compound, a chromium compound, and a hydrocarbon solvent and contacting an olefin with the composition to provide a solution that includes oligomers of the olefin, wherein the solution has a cloud point of less than 75° C.

Embodiment 4. The method of any of the foregoing Embodiments, wherein the alkylaluminum compound includes an irradiated alkylaluminum compound.

Embodiment 5. The method of any of the foregoing Embodiments, wherein the olefin includes ethylene.

Embodiments 6. The method of any of the foregoing Embodiments, further including contacting the olefin and the composition with hydrogen.

Embodiment 7. The method of any of the foregoing Embodiments, wherein the oligomers of the olefin include 1-hexene.

Embodiment 8. The method of any of the foregoing Embodiments, wherein the solution include a polymer.

Embodiment 9. The method of any of the foregoing Embodiments, wherein the polymer is polyethylene.

Embodiment 10. The method of any of the foregoing Embodiments, wherein the polyethylene has a melting point of less than 125.4° C.

Embodiment 11. The method of any of the foregoing Embodiments, wherein the C8-C11 alkane compound having one branch includes an isomer of decane selected from the group consisting of 2-methylnonane, 3-methylnonane, 4-methylnonane, 5-methylnonane, 3-ethyloctane, 4-ethyloctane, and 4-propylheptane.

Embodiment 12. The method of any of the foregoing Embodiments, wherein the solvent includes at least 50%, by volume, of the C8-C11 alkane compound having one branch.

Embodiment 13. The method of any of the foregoing Embodiments, wherein the solvent includes at least 80%, by volume, of the C8-C11 alkane compound having one branch.

Embodiment 14. The method of any of the foregoing Embodiments, wherein the solvent includes at least 50%, by volume, of n-undecane.

Embodiment 15. The method of any of the foregoing Embodiments, wherein the solvent includes at least 90%, by volume, of n-undecane.

Embodiment 16. A method of preparing 1-hexene, including providing a composition that includes an alkylaluminum compound, a chromium compound, and a hydrocarbon solvent and contacting ethylene with the composition to provide a solution that includes 1-hexene and polyethylene, wherein the polyethylene has a melting point of less than 125.4° C.

Embodiment 17. The method of any of the foregoing Embodiments, combined with the method of any other Embodiment.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the methods and systems of the disclosed subject matter without departing from the spirit or scope of the disclosed subject matter. Thus, it is intended that the disclosed subject matter include modifications and variations that are within the scope of the appended claims and their equivalents.

While the disclosed subject matter is described herein in terms of preferred embodiments, those skilled in the art will recognize that various modifications and improvements can be made to the disclosed subject matter without departing from the scope thereof. Moreover, although individual features of some embodiments of the disclosed subject matter can be discussed herein or shown in the drawings of those embodiments and not in other embodiments, it should be apparent that individual features of some embodiments can be combined with one or more features of another embodiment or features from a plurality of embodiments.

What is claimed is:

1. A method of preparing oligomers of an olefin, comprising:
providing a composition comprising an alkylaluminum compound, a chromium compound, and a solvent selected from the group consisting of C8-C11 alkane compounds having one branch, n-undecane, and combinations thereof; and
contacting an olefin with the composition to provide a solution comprising oligomers of the olefin.

2. The method of claim 1, wherein the solution has a cloud point of less than 75° C.

3. A method of preparing oligomers of an olefin, comprising:
providing a composition comprising an alkylaluminum compound, a chromium compound, and a hydrocarbon solvent; and
contacting an olefin with the composition to provide a solution comprising oligomers of the olefin, wherein the solution has a cloud point of less than 75° C.

4. The method of claim 1, wherein the alkylaluminum compound comprises an irradiated alkylaluminum compound.

5. The method of claim 1, wherein the olefin comprises ethylene.

6. The method of claim 1, further comprising contacting the olefin and the composition with hydrogen.

7. The method of claim 1, wherein the oligomers of the olefin comprise 1-hexene.

8. The method of claim 1, wherein the solution comprises a polymer.

9. The method of claim 8, wherein the polymer is polyethylene.

10. The method of claim 9, wherein the polyethylene has a melting point of less than 125.4° C.

11. The method of claim 1, wherein the C8-C11 alkane compound having one branch comprises an isomer of decane selected from the group consisting of 2-methylnonane, 3-methylnonane, 4-methylnonane, 5-methylnonane, 3-ethyloctane, 4-ethyloctane, and 4-propylheptane.

12. The method of claim 1, wherein the solvent comprises at least 50%, by volume, of the C8-C11 alkane compound having one branch.

13. The method of claim 12, wherein the solvent comprises at least 80%, by volume, of the C8-C11 alkane compound having one branch.

14. The method of claim 1, wherein the solvent comprises at least 50%, by volume, of n-undecane.

15. The method of claim 14, wherein the solvent comprises at least 90%, by volume, of n-undecane.

16. A method of preparing 1-hexene, comprising:
providing a composition comprising an alkylaluminum compound, a chromium compound, and a hydrocarbon solvent selected from the group consisting of C8-C11 alkane compounds having one branch, n-undecane, and combinations thereof; and
contacting ethylene with the composition to provide a solution comprising 1-hexene and polyethylene, wherein the polyethylene has a melting point of less than 125.4° C.

17. The method of claim 3, wherein the alkylaluminum compound comprises an irradiated alkylaluminum compound.

18. The method of claim 3, wherein the olefin comprises ethylene.

19. The method of claim 3, further comprising contacting the olefin and the composition with hydrogen.

20. The method of claim 3, wherein the oligomers of the olefin comprise 1-hexene.

21. The method of claim 3, wherein the solution comprises a polymer.

22. The method of claim 21, wherein the polymer is polyethylene.

23. The method of claim 22, wherein the polyethylene has a melting point of less than 125.4° C.

* * * * *